(12) United States Patent
Grodzins

(10) Patent No.: US 6,192,101 B1
(45) Date of Patent: Feb. 20, 2001

(54) X-RAY DETERMINATION OF THE MASS DISTRIBUTION IN CONTAINERS

(75) Inventor: Lee Grodzins, Lexington, MA (US)

(73) Assignee: American Science & Engineering, Inc., Billerica, MA (US)

(*) Notice: Under 35 U.S.C. 154(b), the term of this patent shall be extended for 0 days.

(21) Appl. No.: 09/136,541

(22) Filed: Aug. 19, 1998

Related U.S. Application Data

(60) Provisional application No. 60/056,568, filed on Aug. 21, 1997.

(51) Int. Cl.$^7$ .................................................. G01B 15/02
(52) U.S. Cl. ............................................ 378/55; 378/57
(58) Field of Search ........................................ 378/53–57

(56) References Cited

U.S. PATENT DOCUMENTS

| 5,040,199 | * | 8/1991 | Stein | 378/54 |
| 5,585,603 | * | 12/1996 | Vogeley | 378/54 |

* cited by examiner

Primary Examiner—Craig E. Church
(74) Attorney, Agent, or Firm—Bromberg & Sunstein LLP

(57) ABSTRACT

An apparatus and method for measuring, in a non-invasive manner, the individual mass of objects in containers by means of x-ray transmission radiography in which a beam of penetrating radiation is sent through the container and the transmitted intensity for those photons that interact dominantly via the Compton effect are measured. The masses of the objects in the container are measured with respect to the mass of known objects determined in independent or concurrent measurements.

14 Claims, 3 Drawing Sheets

X-RAY DETERMINATION OF THE MASS DISTRIBUTION IN CONTAINERS

The present application claims priority from U.S. provisional application No. 60/056,568, filed Aug. 21, 1997, which is herein incorporated by reference.

FIELD OF THE INVENTION

This invention relates to the examination of a container by means of penetrating radiation in order to derive the masses of individual objects contained within the container.

BACKGROUND ART

X-ray radiography applied to the non-invasive inspection of the contents of containers is a mature technology carried out by a wide variety of methods. An early purpose of x-ray radiography was to produce a high resolution projected image for visual inspection of the contents. In the past decade, as the purposes of the inspection have become targeted to finding specific contraband such as drugs and explosives, methods of dual energy and backscatter radiography have been developed to measure the atomic number of the objects, as have tomographic techniques to measure the density of the objects and coherent scattering methods to measure the crystalline properties of objects. None of these advances have measured the masses of the objects inside the containers.

There are many instances where it is important to determine, in a non-invasive way, the mass of an object inside a container. For example, the U.S. Customs needs to verify that a container shipped into this country contains the goods described by the container manifest. Because it is impractical to open and examine even a fraction of the millions of containers that enter the country every year, the U.S. treasury loses considerable revenue from high-duty goods that are declared to be low-duty items. The manifest of a container lists the contents by description and weight. It is one purpose of this invention to provide a on-destructive means of verifying that the weights of the items in the container are those declared on the manifest. The invention for measuring masses can be an integral part of the well-used technique of dual-energy analysis so that both the mass and the atomic number of objects can be measured simultaneously to give additional information to compare with the manifest or to find contraband.

SUMMARY OF THE INVENTION

The present invention may be used advantageously to measure, in a non-invasive manner, the individual masses of objects in containers by means of x-ray radiography, to determine the distribution of masses of objects as a function of their position in the container, to determine the dimensional masses—the so-called DIM weights—of odd shapes, from radiographs taken from at least two angles, and to simultaneously measure the mass and the mean atomic number of objects in containers.

In accordance with one aspect of the present invention, in one embodiment, there is provided an apparatus for measuring the mass of one or more objects disposed within a container. Each object has a characteristic mass attenuation factor to penetrating radiation and the mass attenuation factor, which, in particular applications, may or may not be known, is a function at least of the energy of the penetrating radiation. The apparatus has a source of penetrating radiation for generating a beam incident upon the container at a region of incidence and a scanner for causing the region of incidence to traverse a planar projection of the container. Additionally, the apparatus has at least one detector having an output proportional to the intensity of the penetrating radiation traversing the container at the region of incidence, as well as a controller for determining the mass of the at least one object based on the output of the at least one detector and the characteristic mass attenuation factor of the object or objects.

In accordance with alternate embodiments of the present invention, the detector or detectors may include an energy selection arrangement, and the energy selection arrangement may permit analysis of penetrating radiation having energies dominated by Compton scattering. The energy selection arrangement may also permit analysis of penetrating radiation having energies in excess of 60 keV.

In further alternate embodiments of the present invention, the beam may include a fan beam, and may include a pencil beam. Additionally, there may be provided a fiducial mass for intermittent interposition in the beam for normalizing the output of the detector or detectors, and there may be a modulator for alternating interposition of a fiducial mass in the beam.

In accordance with another aspect of the present invention, there is provided a method for measuring the mass of at least one object having a characteristic mass attenuation factor to penetrating radiation, the mass attenuation factor being a function at least of the energy of the penetrating radiation and the object being disposed within a container. The method consists of the steps of generating a beam of penetrating radiation incident upon the container at a region of incidence, scanning the region of incidence such as to traverse a planar projection of the container, detecting the penetrating radiation traversing the container at the region of incidence, producing a detector output proportional to the intensity of the penetrating radiation traversing the container, and determining the mass of the at least one object based on the detector output and the characteristic mass attenuation factor of the at least one object. In accordance with other embodiments of the invention, the method may also include steps of interposing a fiducial mass alternatingly within the beam of penetrating radiation or of discriminating between detected penetrating radiation of energy greater and less than a predetermined discriminant energy. Additionally, the method may include the step of storing the detector output in at least one memory array to produce at least one image.

Where a fiducial mass is intermittently interposed in the beam of penetrating radiation, the step of storing the detector output may include storing the detector output corresponding to an interposed fiducial mass in a first memory array to produce a first image and storing the detector output corresponding to no interposed fiducial mass in a second memory array to produce a second image. The method may also include determining a characteristic atomic number associated with the object or objects.

In accordance with yet another aspect of the present invention, there is provided a method for measuring the mass of an object or of multiple objects, each object having a characteristic mass attenuation factor to penetrating radiation, the mass attenuation factor being a function at least of the energy of the penetrating radiation, the objects being disposed within a container. This method has the steps of generating a beam of penetrating radiation incident upon the container at a region of incidence, scanning the region of incidence such as to traverse a plurality of projections of the container onto a plurality of planes, detecting the penetrating radiation traversing the container at the region of incidence, producing a detector output proportional to the intensity of the penetrating radiation traversing the container, and determining the dimensional mass of the object or objects based on the detector output and the characteristic mass attenuation factor of the object or objects.

BRIEF DESCRIPTION OF THE DRAWINGS

The invention will more readily be understood by reference to the following description taken with the accompanying drawings, in which.

DETAILED DESCRIPTION OF SPECIFIC EMBODIMENTS

Figure 1:
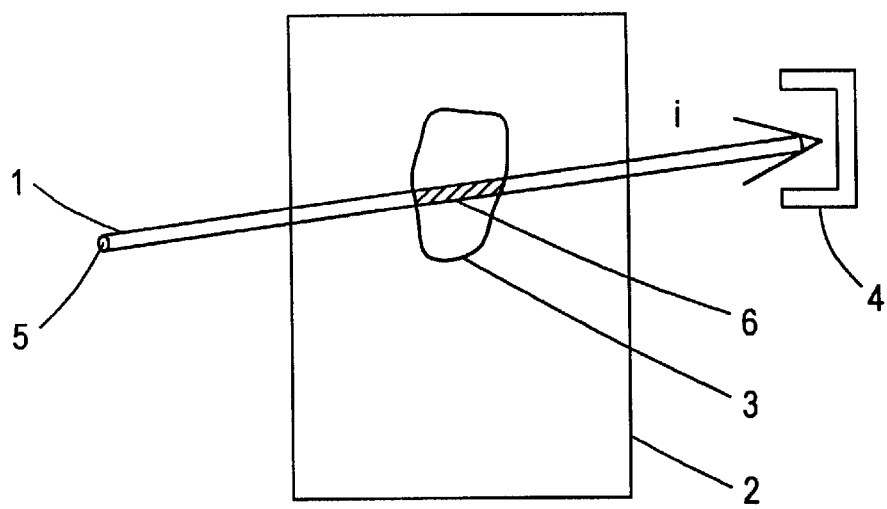
FIG. 1 is a diagram of the basic principles of a prior art x-ray system.

Referring now to FIG. 1, the main components of a radiography system based on the transmission of penetrating radiation are shown. A beam 1 of penetrating radiation, which may be, for example, a beam of x-rays such as a monochromatic x-ray beam of energy E, is produced by a source (not shown), and has an intensity $I_0$ and typical cross sectional area 5, passes through an object 3 that is in a container 2. Beam 1 will be referred to in the present description, without limitation, as an x-ray beam. The intensity $I_i$ of the x-ray beam emerging from the container at a particular point i is measured in the detector 4.

For the purposes of the explanation, it is assumed that the object 3 has uniform density $\rho$ and that the beam has uniform intensity through its cross section 5. Neither condition is necessary for the practice of the invention. The cross sectional area 5 of beam 1 is small compared with the dimensions of object 3.

The intensity $I_i$ of the beam that emerges from the object 3 is related to the intensity $I_0$ of the beam entering the object by the well-known relationship, $$I_i = I_0 \exp[-(\mu \rho d_i)_3], \quad \quad 1)$$

where $\mu$ is the mass attenuation factor for the object 3 and $d_i$ is the length of the beam path in the object.

Taking the logarithm of both sides of Equation 1, $$\text{Log }(I_0/I_i) = (\mu \rho d_i)_3. \quad \quad 2)$$

Multiplying both sides of Equation 2 by the area $\alpha$ of the X-ray beam, produces:

$$\alpha \text{Log }(I_0/I_i) = (\mu \rho d_i)_{3\ \alpha}. \quad \quad 3)$$

The right hand side of Equation 3 is just the product of $\mu$ times the mass $m_i$ of the material along x-ray path i through object 3, since $(d_{i\ \alpha})$ is just the volume 6 of object 3 that is traversed by x-ray beam 1 along path i, and the density $\rho$ is just the mass per unit volume of the material that makes up the object. Thus, $$\alpha \text{ Log }(I_0/I_i) = (\mu \rho d_i)_{3\ \alpha = \mu m_i}, \quad \quad 4)$$

where $m_i$, as stated above, is the mass of the material contained within volume 6 traversed by the x-ray beam.

As x-ray beam 1 scans over the entire face of the object, the quantities $[\alpha \text{Log }(I_0/I_i)]$ are summed. The total sum over the entire face is $$\Sigma \alpha \text{ Log }(I_0/I_i) = \Sigma \mu m_i = \mu M, \quad \quad 5)$$

where M is the total mass of object 3.

Energy Conditions.

The total sum over the object, i.e. the left hand side of Equation 5, only gives a unique measure of M if mass attenuation $\mu$ is known. The values of $\mu$ are strongly material-dependent for x-ray energies where the photoelectric effect is significant. When these lower x-ray energies are used then Equation 5 does not give a measure of the mass of an unknown object. An example illustrates the point: If the x-ray energy has an average energy of 80 keV, the typical average energy for x-ray scanners of airport luggage, then a one pound piece of iron would have almost four times the attenuation of a one pound book. This invention uses independent knowledge of the behavior of $\mu$, such as operation within an energy regime where x-rays interact with matter predominantly through the Compton effect.

The mass attenuation factor can be written as the sum of the mass attenuation factors for the Compton interaction, the Rayleigh or coherent interaction, the photo electric interaction and the pair production interaction:

$$\mu = \mu_c(\text{Compton}) + \mu_R(\text{Rayleigh}) + \mu_{pe}(\text{photo electric}) + \mu_{pp}(\text{pair}). \quad \quad 6)$$

When the X-ray beam energies are sufficiently high that the Rayleigh and photo electric terms are negligible, but still low enough that the pair production term is negligible, then Equation 6 simplifies to $$\mu = \mu_c(\text{Compton}). \quad \quad 7)$$

Figure 2:
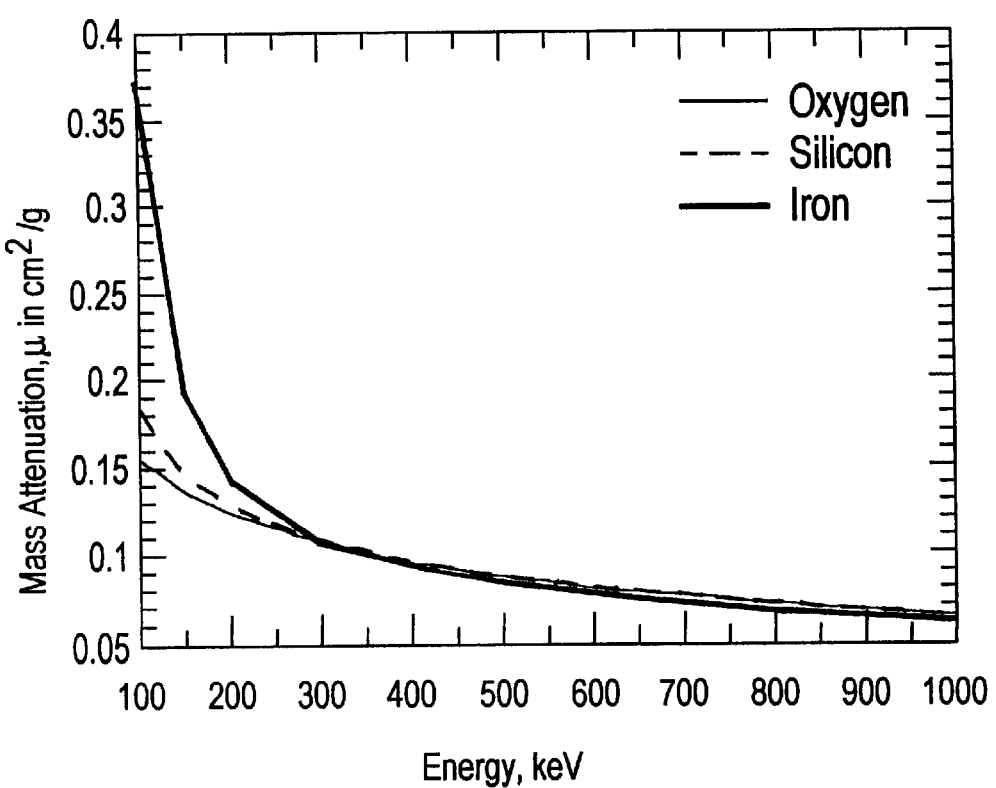
FIG. 2 is a graph of the total mass absorption coefficients versus energy for three substances, oxygen, silicon and iron, to show that above about 300 keV, the coefficients are independent of the substance and are only slowly varying functions of the x-ray energy.

Referring now to FIG. 2, a graph is presented of the total mass absorption coefficients versus energy for three substances, oxygen, silicon and iron. It is evident that above about 300 keV, the coefficients are independent of the substance and are only slowly varying functions of the x-ray energy. When the container being inspected is known only to contain low atomic number material, such as plastics or foodstuffs, the x-ray energies can be anywhere in the range from about 60 keV to as much as 2,000 keV. When inspecting cargo containers that are likely to contain metals such as iron or brass, the x-ray energies may be in the range from about 250 keV to 1500 keV where the mass attenuation due to other constituent processes becomes negligible, as shown in FIG. 2. If the material in question is very high Z, such as tungsten or lead, then the x-ray energies should be in the range of 1 MeV to 2 MeV.

The Compton mass attenuation coefficient $\mu_c$, is nearly independent of material, as can be seen from its explicit expression:

$$\mu_c = \sigma_e(Z/A)N_0. \quad \quad 8)$$

The first factor, $\sigma_e$, is the probability for interaction with a single electron and is independent of material. The last factor, $N_0$, is a constant, Avogadro's number. The second factor, (Z/A), the number of electrons per atomic or molecular mass equals 0.5 for most elements from helium to calcium. Substances that contain hydrogen usually have higher values; Z/A for water is 0.55. Heavier metals have lower values; Z/A for iron is 0.46. This 10% variation around the mean sets the limit to the accuracy of the mass determination if nothing else is known about the material. For the application where a shipping manifest is being verified, the material is presumed to be known so that the precise value of $\mu$ can be used and there is no uncertainty to the measurement caused by the variation of $\mu$ with material.

The Compton mass attenuation $\mu_c$, depends on the energy of the x-ray since $\sigma_e$ varies with energy. The variation of $\mu_{total}$ with energy and element is shown in FIG. 2 for oxygen (Z=8), silicon (Z=14) and iron (Z=26) over the energy range from 100 keV to 1 MeV. Above 300 keV, the values of the total mass attenuation coefficients are essentially the same for the three elements; even at 200 keV, the photoelectric effect influences the total mass attenuation at below the 15% level. Above 300 keV, the $\mu$ values slowly decrease. Energy variation in $\mu_c$ can be completely eliminated, for example, by using a monoenergetic beam of gamma-rays from a radioactive source, which may be practical for situations when the speed of examination is not critical and there is no prohibition about the use of radioactivity. For many applications, however, an x-ray tube that emits an intense spectrum of x-rays is needed. If the energy distribution can be directly measured, for example, by pulse counting, then its effect can be unequivocally assessed. If the energy distribution is not measured then there are several ways of accounting for its effect: A simple method is to use the functional dependence of the energy spectrum on the amount of absorption to adjust the $\mu$ values. This procedure may be accurate if the contents are known, but it has 10% to 20% uncertainties if the contents of the container are unknown. A second method is to reduce the energy variation of the spectrum by appropriate absorbers, a method that reduces the uncertainties to well below the 10% level but has the disadvantage of reducing the measured x-ray flux. A third method, in accordance with a preferred embodiment of the invention, may be used for the case of inspecting unknown contents, entails normalizing every pixel value by a known fiducial mass that is measured concurrently with the contents of the container.

When the energy dependence is taken into account, then Equation 5 yields the total mass of object 3.

Other Dependencies.

Equation 5 applies to an object of arbitrary shape and arbitrary orientation with respect to the x-ray beam. Equation 5 also applies to a non-uniform x-ray beam; that is, one whose intensity is not uniform over its cross section and may vary as a function of x-ray beam position. If these spatial non-uniformities are stable over time and position, they can be accounted for by determining the non-uniformities in independent measurements, storing the results in a look-up table, and factoring the results into the analysis to adjust the measured intensities.

A further problem that must be addressed is the sparseness or redundancy of the coverage of the x-ray inspection of an object. In general, one does not expect the x-ray coverage of the object to be uniform since, in some embodiments, there is relative motion between the object and the beam and that motion introduces its own non-uniformities. (The clear exception is a batch-mode inspection in which a broad beam of x-rays is sent through the stationary object into a large area detector.) In a preferred embodiment of the invention, the object is passed through a fan or rastered-pencil beam of x-rays. In various cases, either gaps or, more likely, overlap, in the x-ray coverage of the object result.

To account for the non-uniform beam coverage it may be practical in many applications to normalize the results by scaling factors determined in independent measurements of known masses. The normalizing tests may be carried out periodically, including tests of known masses carried out between every inspection of an unknown container. The most precise normalization is that carried out by inserting a known mass concurrently with the measurement. Normalizing the intensities with concurrent measurements of a known mass has the advantage of adjusting for temporal and spatial non-uniformities, such as variations in the intensity of the x-ray beam as functions of cross sectional area, position and time. There are many specific ways of carrying out concurrent normalization but all have in common that a known mass (or masses) is inserted into the beam when the object is being examined. In a preferred embodiment, a known mass is rotated in and out of the x-ray beam many times a second. Two images are formed, one with the fiducial mass in the beam, one with it out of the beam. Subtracting the logarithms of the intensities of the two images produces a fiducial image of the known mass obtained with an energy spectrum that is the essentially the same as that used to interrogate the unknown mass. The absorption image obtained for the unknown mass is then a simple function of the absorption image obtained for the known mass.

Embodiment Using a Fan Beam.

Figure 3:
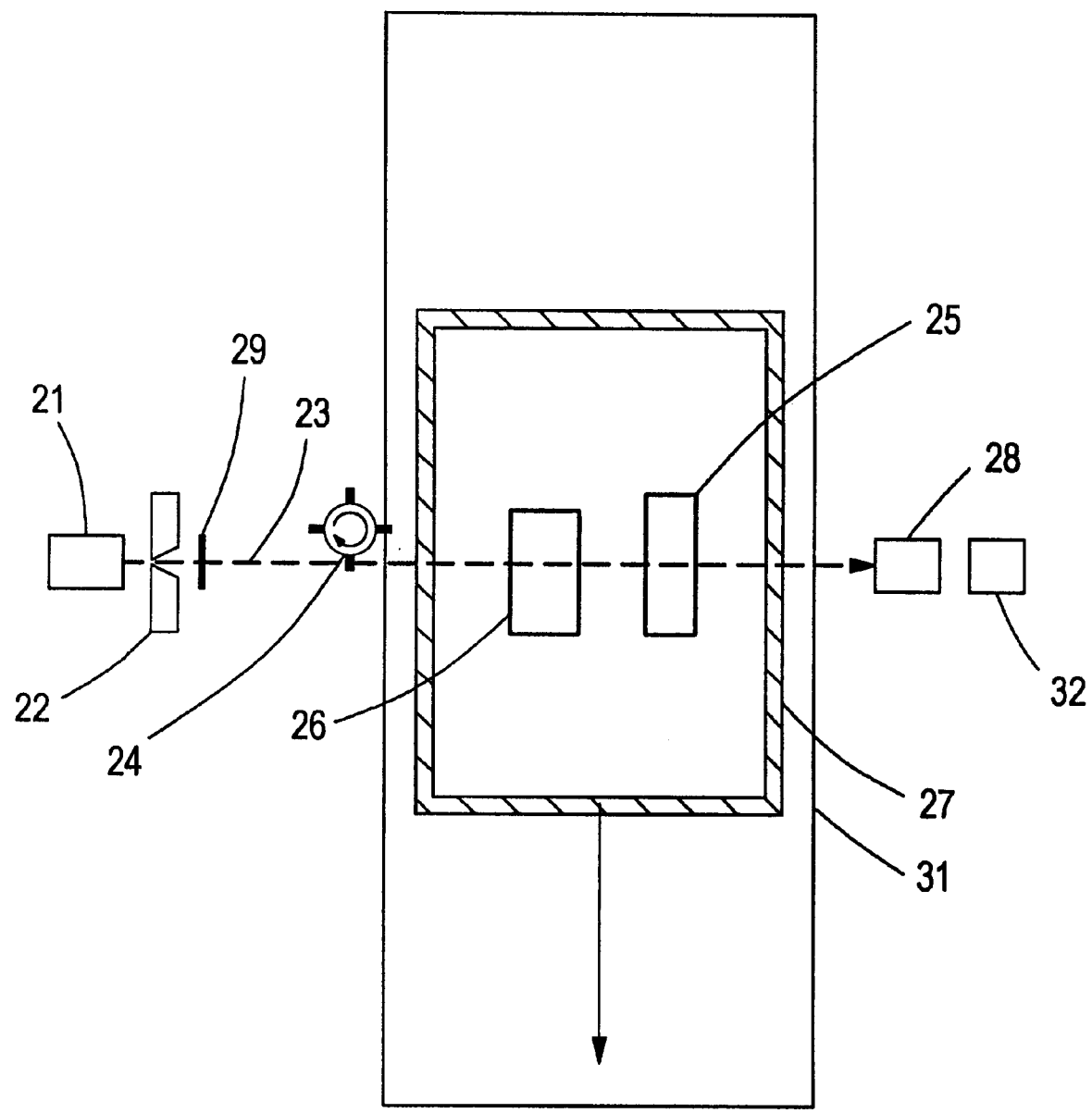
FIG. 3 is a top-view sketch of the basic components using a fan beam of x-rays to measure the masses of objects with respect to a fiducial mass that is rotated in and out of the x-ray beam. The container is carried through the fan beam by a conveyor.

Referring now to FIG. 3, x-rays created in an x-ray generator 21 are collimated by slits 22 into a fan beam 23. Beam 23 passes through objects 25 and 26 in a container 27, and is measured in a detector array 28. Container 27 is carried through the fan beam by a conveyor 31. An absorber 29 may be placed in the beam to suppress lower energy x-rays. A rotating fiducial mass 24 may be placed in the beam for normalization. A second detector array 32 may be placed behind or beside detector array 28 to measure the intensities of the x-rays in two energy regimes. As an example, container 27 may typically have dimensions of 6 meters long, 2 meters high, and 2 meters wide, moving at 10 cm per second through the x-ray fan beam 23, taking 1 minute for a full inspection. The fan beam is typically on the order of 5 mm wide. The detector array 28 is typically 3 meters high, with 600 detectors, each with a cross section of 5 mm×5 mm perpendicular to the beam. The x-ray generator typically has a maximum potential of 450 keV. Detector 28 is highly efficient for counting x-rays greater than 200 keV. The absorber 29 may be placed in the beam to suppress x-ray energies below 150 keV. The fiducial mass 24 is rotated in and out of the fan beam 23 so that it is alternatingly in and out of the beam for periods on the order of $\frac{1}{40}$ of a second.

As the container moves through the fan beam, the current in each of the detectors is integrated each $\frac{1}{40}$ of a second, corresponding to 2.5 mm of container travel. The integrated signals corresponding to measurements with mass 24 in and out of the beam are stored in separated memory arrays to produce two images, one with and one without the fiducial mass. "Image," as used in this description and in any appended claims, refers to a representation, whether fixed or otherwise, of data corresponding to multiple spatial positions. Subtracting the logarithms of the intensities obtained with and without 24, called log $I_{24}$ and log I, respectively—or equivalently, dividing the intensities—yields the absorption for the known normalizing mass, $M_N$. The mass of the material that the fan x-ray beam has passed through is just the ratio $$M = M_N (\log I)/[\log I_{24} - \log I] \quad (9)$$

The mass M can be summed over a given object or a group of objects by appropriate deconvolution of the transmission image. A much-used method for doing this uses edge-finding algorithms to determine the boundaries of images that exhibit constant or slowly varying intensities over significant areas. Overlapping projected areas are disentangled by subtracting the logarithms of intensities of these areas to yield the x-ray absorption, and hence the mass of the individual objects.

Embodiment Using a Rastered Pencil Beam.

Figure 4:
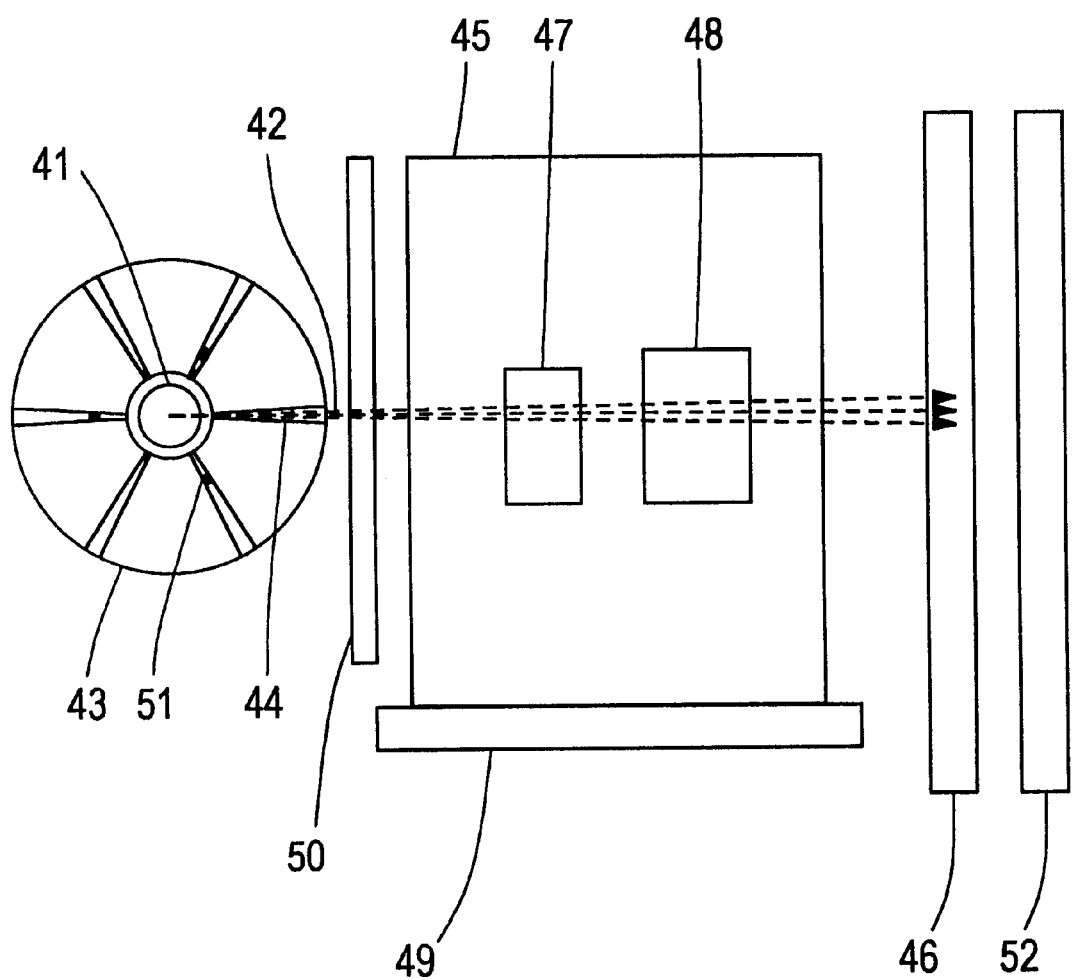
FIG. 4 is a sketch of the basic components using a raster scanned beam of x-rays to measure the masses of objects in a container. Fiducial masses are placed in alternate spokes of the rotating wheel. The container is carried through the rastered pencil beam by a conveyor.

Referring now to FIG. 4, the x-rays, created in an x-ray generator 41 are formed into a rastering pencil beam 42 by means of a rotating wheel 43 with hollow spokes 44 through which the x-ray beam passes. As the wheel 43 rotates, the x-ray beam 42, emerging from the rotating spoke 44, is swept across the container 45 into the detector 46. The container is carried through the fan beam by a conveyor 49. Two objects 47 and 48 are in the container 45. An absorber 50 may be placed in the x-ray beam path to harden the x-ray spectrum. Fiducial mass 51 is placed in alternate spokes for normalization. A second detector 52 may be placed behind detector 46 so that intensities of the x-rays may be measured separately in two energy regimes, in one of which the dominant material interaction is the Compton effect. Thus, detector 46 may be sensitive to a broad spectrum of x-ray energies, which detector 52 may be sensitive only to harder (higher energy) x-rays.

The parameters of container size and speed of inspection may be similar to those presented above in reference to FIG. 3, for exemplary purposes. The spatial definition is now defined by the area of pencil beam 42. The spoked wheel 43 has six spokes 44 in this embodiment so that six sweeps of the container are obtained per revolution of wheel 43. The method of measuring the masses of the objects 47 and 48 is essentially the same as that using a fan beam.

The primary difference between an embodiment employing a pencil beam and embodiment employing a fan beam is that the spatial resolution in the pencil beam case is defined by the slits in the spokes, which in this example have an opening of 2.5 mm×2.5 mm. The wheel is rotating at 400 rpm so that each sweep takes 1/40th of a second. Identical fiducial masses 51 are placed in alternate spokes so that two transmission images are formed of the container, one with and one without the fiducial masses in the beam. In effect, the beam samples the container in stripes, 2.5 mm wide, with gaps of 2.5 mm. The analysis to obtain the masses of the individual objects 47 and 48 is the same as that for the fan beam.

One objective of this patent is to measure the masses of the objects inside the container by measuring the attenuation with x-ray beams that interact with the contents through the Compton interaction since that interaction is closely independent of the unknowns such as the nature of the material, the energy spectrum above 200 keV and the degree of beam hardening. The method can be combined with a second transmission measurement to obtain a measure of the atomic number of the articles in the container. The dual energy methods for doing this are well known and much used for finding the mean atomic number of articles in small containers such as suitcases.

Embodiment Using Dual Energy to Obtain Both M and z.

The combined information of the atomic number Z and the mass M for each object in a container is a more effective identifier than the mass alone. Two distinct methods for measuring both are described. The first, applicable to small containers with only moderate x-ray attenuation uses lower x-ray energies, from about 50 keV to 400 keV. The second, applicable to large containers with large, heavy objects, uses high x-ray energies, from 300 keV to at least 2 MeV and preferably to at least 3 MeV.

1. Lower energies, small containers. The atomic number information Z is obtained from so-called dual-energy analysis, used extensively, for example by x-ray systems used to inspect luggage at airports. Two transmission images are obtained. One is at an energy where the Compton effect dominates and the intensities are almost independent of the atomic number; that is, Equation 7 is approximately satisfied. The second image is obtained at x-ray energies of 60 keV to 80 keV; the lower the x-ray energy, the more the interaction is dominated by the photoelectric effect and the more sensitive is the absorption to the Z of the material. The ratio of the logarithms of the transmission intensity obtained at high energy to the transmission intensity obtained at low energies is directly related to the atomic number of the object, and independent of its density and mass. The requirement that the lower x-ray energy be well below 100 keV, limits the usefulness of the method to smaller containers such as luggage and small packages. When the conditions for the application of this mode of dual energy are realizable, then we propose to use the higher x-ray energy to measure the mass of the object and the dual energy method to obtain the Z of the object.

2. High energies, large containers. The atomic number information Z of an object can also be obtained by a dual energy method that combines a transmission image in which the pair production interaction is significant with one obtained at lower energies where the pair production interaction is negligible. Since the pair production cross section depends on the square of the atomic number, while the Compton cross section depends linearly on the atomic number, the ratio of the logarithms of the intensities of the two measurements is proportional to the atomic number of the object. The dual energy method can be realized when the higher x-ray energies are greater than about 3 MeV, while the lower x-ray energies are below about 1.5 MeV. We propose to use the lower of the two transmission images to obtain the mass of the objects and the ratio of the two transmission images to obtain the atomic number of the two objects.

Embodiment Using More than One View.

If quantitative transmission images are obtained from more than one direction, then it will be easier to measure the individual masses, since a cluttered view in one direction may appear relatively uncluttered in another, for example orthogonal, direction.

The described embodiments of the invention are intended to be merely exemplary and numerous variations and modifications will be apparent to those skilled in the art. All such variations and modifications are intended to be within the scope of the present invention as defined in the appended claims.

I claim:

1. An apparatus for measuring the mass of at least one object having a characteristic mass attenuation factor to penetrating radiation, the mass attenuation factor being a function at least of the energy of the penetrating radiation, the object being characterized by an unknown composition and being disposed within a container, the apparatus comprising:

a. a source of penetrating radiation for generating a beam incident upon the container at a region of incidence;

b. a scanner for causing the region of incidence to traverse a planar projection of the container;

c. at least one detector having an output proportional to the intensity of the penetrating radiation traversing the container at the region of incidence;

d. an energy selection arrangement permitting analysis of penetrating radiation having energies dominated by Compton scattering; and e. a controller for determining the mass of the at least one object based on the output of the at least one detector, independently of knowledge of the composition of the at least one object.

2. An apparatus according to claim 1, where the at least one detector includes the energy selection arrangement.

3. An apparatus according to claim 1, further comprising a modulator for alternating interposition of a fiducial mass in the beam.

4. An apparatus according to claim 1, wherein the energy selection arrangement permits analysis of penetrating radiation having energies in excess of 60 keV.

5. An apparatus according to claim 1, wherein the beam includes a fan beam.

6. An apparatus according to claim 1, wherein the beam includes a pencil beam.

7. An apparatus according to claim 1, further comprising a fiducial mass for intermittent interposition in the beam for normalizing the output of the at least one detector.

8. A method for measuring the mass of at least one object having a characteristic mass attenuation factor to penetrating radiation, the mass attenuation factor being a function at least of the energy of the penetrating radiation, the object being disposed within a container, the method comprising:

a. generating a beam of penetrating radiation incident upon the container at a region of incidence;

b. scanning the region of incidence such as to traverse a planar projection of the container;

c. selecting a range of energies of penetrating radiation dominated by Compton scattering for detection;

d. detecting the penetrating radiation traversing the container at the selected range of energies at the region of incidence;

e. producing a detector output proportional to the intensity of the penetrating radiation traversing the container; and f. determining the mass of the at least one object based on the detector output.

9. A method according to claim 8, further comprising the step of storing the detector output in at least one memory array to produce at least one image.

10. A method according to claim 9, further comprising the step of interposing a fiducial mass alternatingly within the beam of penetrating radiation.

11. A method according to claim 9, further comprising the step of discriminating between detected penetrating radiation of energy greater and less than a predetermined discriminant energy.

12. A method according to claim 11, further comprising the step of determining a charateristic atomic number associated with the at least one object.

13. A method according to claim 10, further comprising the step of storing the detector output in at least one memory array to produce at least one image.

14. A method according to claim 13, wherein the step of storing the detector output includes storing the detector output corresponding to an interposed fiducial mass in a first memory array to produce a first image and storing the detector output corresponding to no interposed fiducial mass in a second memory array to produce a second image.

* * * * *